United States Patent [19]

Barlow et al.

[11] Patent Number: 5,783,453

[45] Date of Patent: Jul. 21, 1998

US005783453A

[54] NON-SEPARATION SPECIFIC BINDING CHEMILUMINESCENT ASSAY

[75] Inventors: Eve H. Barlow, Holliston; Eddie Carroll, III, Waltham; Joseph E. Connolly, Dedham; Michael J. Lee, Sherborn; Richard A. Martinelli, Brighton; John T. Unger, Medfield, all of Mass.

[73] Assignee: Chiron Diagnostics Corporation, East Walpole, Mass.

[21] Appl. No.: 496,549

[22] Filed: Jun. 29, 1995

[51] Int. Cl.$^6$ ............... G01N 33/543; G01N 33/551; G01N 33/553; C12G 1/00

[52] U.S. Cl. ............... 436/518; 436/523; 436/524; 436/525; 436/526; 435/4; 435/6; 435/7.2; 435/7.9; 435/7.91; 435/7.92; 435/7.93; 435/7.94; 435/7.95

[58] Field of Search ............... 435/4, 6, 7.2, 7.9, 435/7.95, 975, 968; 436/518, 523–526

[56] References Cited

U.S. PATENT DOCUMENTS

| | | | |
|---|---|---|---|
| 3,352,791 | 11/1967 | Sheehan et al. | |
| 3,689,391 | 9/1972 | Ullman | 204/159 |
| 4,277,437 | 7/1981 | Maggio | 422/61 |
| 4,554,088 | 11/1985 | Whitehead et al. | 252/62.54 |
| 4,563,419 | 1/1986 | Ranki et al. | 435/6 |
| 4,576,912 | 3/1986 | Yaverbaum et al. | 435/7 |
| 4,628,037 | 12/1986 | Chagnon et al. | 436/526 |
| 4,672,040 | 6/1987 | Josephson | 436/526 |
| 4,695,392 | 9/1987 | Whitehead et al. | 252/62.54 |
| 4,695,393 | 9/1987 | Whitehead et al. | 252/62.54 |
| 4,698,302 | 10/1987 | Whitehead et al. | 435/94 |
| 4,761,382 | 8/1988 | Woodhead et al. | 436/536 |
| 4,927,769 | 5/1990 | Chang et al. | 436/518 |
| 5,017,473 | 5/1991 | Wagner | 435/7.92 |
| 5,053,326 | 10/1991 | Renz | 435/6 |
| 5,093,270 | 3/1992 | Chang et al. | 436/518 |
| 5,241,070 | 8/1993 | Law et al. | 546/107 |
| 5,321,136 | 6/1994 | McCapra | 546/104 |
| 5,395,752 | 3/1995 | Law et al. | 435/6 |

FOREIGN PATENT DOCUMENTS

| | | |
|---|---|---|
| 063852A3 | 11/1982 | European Pat. Off. |
| 0 309 230 | 3/1989 | European Pat. Off. |
| 0 425 217 A2 | 5/1991 | European Pat. Off. |
| 476545A1 | 3/1992 | European Pat. Off. |
| 0 481 704 A1 | 4/1992 | European Pat. Off. |
| 515194A3 | 11/1992 | European Pat. Off. |
| 61217766 | 9/1986 | Japan . |
| 89/02896 | 4/1989 | WIPO . |
| 93/01308 | 1/1993 | WIPO . |
| 94/21823 | 9/1994 | WIPO . |

OTHER PUBLICATIONS

Arnold, Lyle J., Jr. et al. "Assay Formats Involving Acridinium–Ester–Labeled DNA Probes", *Clin. Chem.*, vol. 35/8, pp. 1588–1594 (1989).

Septak, M., "Acridinium Ester–labelled DNA Oligonucleotide Probes", *Journal of Bioluminescence and Chemiluminescence*, vol. 4, pp. 351–356 (1989).

Weeks, I. et al., "Acridinium Esters as High–Specific–Activity Labels in Immunoassay", *Clin. Chem.*, vol. 29/8, pp. 1474–1479 (1983).

*Primary Examiner*—Sheela Huff
*Attorney, Agent, or Firm*—Arthur S. Morgenstern; Leona L. Lauder; Robert P. Blackburn

[57] ABSTRACT

The assay described herein is predicated on an observation that when acridinium ester labeled tracers are bound to their corresponding binding conjugate immobilized on a metal oxide solid phase, the measurable chemiluminescent light emission of the labeled tracer bound to the solid phase is quenched as compared to the free fraction tracer that is unattached to the solid phase. According to the invention, a non-separation specific binding assay to detect or quantify the presence of an analyte is provided where the entire reaction mixture is flashed (including unreacted tracer) and modulated signal (because of the quench effect) is associated with a reference, thus determining the amount or presence of said analyte in said sample. Disadvantages inherent in heterogeneous assays employing multiple separations may be avoided using this non-separation method.

22 Claims, 5 Drawing Sheets

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 70
        ( B ) TYPE: nucleic acid
        ( C ) STRANDEDNESS: single
        ( D ) TOPOLOGY: linear ( i i ) MOLECULE TYPE: Nucleic acid probe, PM979,
        having a portion complementary to a Salmonella specific
        target sequence, where bases 1-10 constitute a spacer
        arm, bases 11-46 consist of the 5' sequence of the
        nanovariant (+) template, and bases 47-70 are
        complementary to the Salmonella specific target
        sequence.

( i i i ) HYPOTHETICAL: No ( i v ) ANTI-SENSE: No ( v ) SEQUENCE DESCRIPTION: SEQ ID NO: 1:

CCTAGTCCAA GGGGAAATCC TGTTACCAGG ATAACGGGGT 40

TTTCTCATAA GCGCCATTGA TGTTGTCGCC 70

( 2 ) INFORMATION FOR SEQ ID NO: 2:

( i ) SEQUENCE CHARACTERISTICS:
        ( A ) LENGTH: 95
        ( B ) TYPE: nucleic acid
        ( C ) STRANDEDNESS: single
        ( D ) TOPOLOGY: linear ( i i ) MOLECULE TYPE: Nucleic acid probe, MASA5, having a
        portion complementary to a Salmonella specific target
        sequence, where bases 1-10 constitute a spacer arm,
        bases 11-71 consist of the 5' sequence of the midivariant
        ( + ) template, and bases 72-95 are complementary to the
        Salmonella specific target sequence.

( i i i ) HYPOTHETICAL: No ( i v ) ANTI-SENSE: No ( v ) SEQUENCE DESCRIPTION: SEQ ID NO: 2:

| | | | | |
|---|---|---|---|---|
| CCTAGTCCAA | GGGGACCCCC | CGGAAGGGGG | GACGAGGTGC | 40 |
| GGGCACCTCG | TACGGGAGTT | CGACCGTGAC | AGGTCAACTG | 80 |
| AACGCCCTGA | GCTTT | | | 95 |

( 2 ) INFORMATION FOR SEQ ID NO: 3:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Nucleic acid probe, PM1076, half of the
        Salmonella target, complementary to PM979 and MASA5,
        defined herein.

( i i i ) HYPOTHETICAL: No ( i v ) ANTI-SENSE: No ( v ) SEQUENCE DESCRIPTION: SEQ ID NO: 3:

| | | | |
|---|---|---|---|
| GGCGACAACA | TCAATGGCGC | TTAT | 24 |

( 2 ) INFORMATION FOR SEQ ID NO: 4:

( i ) SEQUENCE CHARACTERISTICS:
        ( A ) LENGTH: 48
        ( B ) TYPE: nucleic acid
        ( C ) STRANDEDNESS: single
        ( D ) TOPOLOGY: linear ( i i ) MOLECULE TYPE: Nucleic acid probe, PM2058, a Salmonella
        target, complementary to PM979 and MASA5, defined herein.

( i i i ) HYPOTHETICAL: No ( i v ) ANTI-SENSE: No ( v ) SEQUENCE DESCRIPTION: SEQ ID NO: 4:

| | | | | |
|---|---|---|---|---|
| GGCGACAACA | TCAATGGCGC | TTATAAAGCT | CAGGGCGTTC | 40 |
| AGTTGACC | | | | 48 |

( 2 ) INFORMATION FOR SEQ ID NO: 5:

( i ) SEQUENCE CHARACTERISTICS:
        ( A ) LENGTH: 48
        ( B ) TYPE: nucleic acid
        ( C ) STRANDEDNESS: single
        ( D ) TOPOLOGY: linear ( i i ) MOLECULE TYPE: Nucleic acid probe, SA7, an anti-Salmonella
        target.

( i i i ) HYPOTHETICAL: No ( i v ) ANTI-SENSE: No ( v ) SEQUENCE DESCRIPTION: SEQ ID NO: 5:

| | | | | |
|---|---|---|---|---|
| GGTCAACTGA | ACGCCCTGAG | CTTTATAAGC | GCCATTGATG | 40 |
| TTGTCGCC | | | | 48 |

( 2 ) INFORMATION FOR SEQ ID NO: 6:

( i ) SEQUENCE CHARACTERISTICS:
  ( A ) LENGTH: 24
  ( B ) TYPE: nucleic acid
  ( C ) STRANDEDNESS: single
  ( D ) TOPOLOGY: linear ( i i ) MOLECULE TYPE: Nucleic acid probe, MD24, complementary to bases 34-57 of the midivariant (+) template; i.e. bases 44-67 of MASA5, defined herein.

( i i i ) HYPOTHETICAL: No ( i v ) ANTI-SENSE: No ( v ) SEQUENCE DESCRIPTION: SEQ ID NO: 6:

ACGGTCGAAC TCCCGTACGA GGTG                                      24

( 2 ) INFORMATION FOR SEQ ID NO: 7:

( i ) SEQUENCE CHARACTERISTICS:
    ( A ) LENGTH: 282
    ( B ) TYPE: nucleic acid
    ( C ) STRANDEDNESS: single
    ( D ) TOPOLOGY: linear ( i i ) MOLECULE TYPE: Nucleic acid probe, MDV-SA2 RNA Transcript, where bases 1-61 consist of the 5'end of the midivariant (+) template, bases 62-69 and 118-123 are plasmid linker sequences, bases 70-117 are complementary to a Salmonella specific target sequence, and bases 124-282 consist of the 3'end of the midivariant (+) template.

( i i i ) HYPOTHETICAL: No ( i v ) ANTI-SENSE: No ( v ) SEQUENCE DESCRIPTION: SEQ ID NO: 7:

GGGGACCCCC CGGAAGGGGG GACGAGGUGC GGGCACCUCG                      40
UACGGGAGUU CGACCGUGAC GAGCCUCGAG GCGACAACAU                      80
CAAUGGCGCU UAUAAAGCUC AGGGCGUUCA GUUGACCUCG                     120
AGGAGUCACG GGCUGCGCUU UCGCGCAUCU CCCAGGUGAC                     160
GCCUCGAGAA GAGGCGCGAC CUUCGUGCGU UUCGGCGACG                     200
CACGAGAACC GCCACGCUGC UUCGCAGCGU GGCCCCUUCG                     240
CGCAGCCCGC UGCGCGAGGU GACCCCGAA GGGGGGUUCC                      280
CC                                                             282

NON-SEPARATION SPECIFIC BINDING CHEMILUMINESCENT ASSAY

FIELD OF THE INVENTION

This invention relates to a non-separation chemiluminescent specific binding assays.

DEFINITIONS

As used herein "analyte" is defined as any substance capable of undergoing a binding reaction with one or more specific binding partners. The term "analyte" encompasses, but is not limited to, serum proteins, hormones, drugs, antigens, antibodies (including monoclonal, polyclonal, and fragments thereof), pathogens, enzymes, metabolites, coenzymes and their binding partners, polynucleotides, oligonucleotides, hybrids of polynucleotide or oligonucleotides, and metals and chelating agents thereto. "Specific binding partner" is defined as a substance capable of binding to the targeted analyte and an analyte analogue. The term "specific binding partner" encompasses, but is not limited to, antibodies, antigens, avidin, biotin, thyroxin, thyroxin-binding globulin, polysaccharide, phosphorylcholine, aminoethyldihydrogen phosphate residues, estrogen, vitamin B-12 intrinsic factor, binding proteins, mixtures thereof, and various other proteins and peptides including oligonucleotides and so on. "Analyte analogue" is defined as a substance that is capable of pairing with the selected specific binding partner of the targeted analyte through a specific binding reaction. "Specific binding complex" refers either to a complex of the targeted analyte-specific binding partner, a complex of the analyte analogue-specific binding partner, or a complex of a first specific binding partner-targeted analyte-second specific binding partner "sandwich" (where the first and second binding partners may be the same or different). The "specific binding complex" may be formed by any number of specific binding reactions including immunological, chemical, and complementary binding. "Tracer" is defined as a labeled specific binding partner, a labeled analyte, or a labeled analyte analogue. "Binding conjugate" is defined as a binding moiety that may be selected from the analyte, analyte analogue, or specific binding partner of the analyte. "Free fraction" is defined as components of the assay that are not attached to the solid phase.

BACKGROUND OF THE INVENTION

As is well known in the art, compounds that provide a chemiluminescent signal are currently utilized as labels in specific binding assays. Both separation (heterogeneous) and non-separation (homogeneous) assays have been prepared using chemiluminescent compounds as labels.

Heterogeneous assays generally refer to assays that require a separation of the specific binding complex formed on a solid phase from the free fraction prior to activating and measuring the chemiluminescent flash. Thus, typically, heterogeneous assay protocol requires several steps of separation of the solid phase reaction product from the free fraction, where decanting and resuspension in water is typically required. These separation step(s) associated with heterogeneous assays occupy a significant amount of time and increase the chance of operator error.

Homogeneous assays generally refer to assays that typically do not require physical separation of the solid phase reaction binding complex and free fraction prior to activating and measuring the chemiluminescent flash. For example, U.S. Pat. No. 5,017,473 describes a separation free solid phase immunoassay utilizing light absorbing material (a dye), where the material is described as absorbing all of the chemiluminescence except that associated with the bound tracer whereby the only emission detected is due to the bound tracer.

Alternative assay systems that eliminate the need of separating the solid phase binding complex from the free fraction are needed.

SUMMARY OF THE INVENTION

The assay described herein is predicated on an observation that when acridinium ester labeled tracers are bound to their corresponding binding conjugate immobilized on a metal oxide solid phase, the measurable chemiluminescent light emission of the labeled tracer bound to the solid phase is reduced (referred to herein as "quenched") as compared to the chemiluminescent signal generated from the tracer that remains in the free fraction unattached to the solid phase.

According to the invention, a non-separation specific binding assay to detect or quantify the presence of an analyte in a sample is provided, said assay comprising: contacting said sample with a solid phase comprising a metal oxide having attached thereto a binding conjugate and a tracer comprising an acridinium or benzacridinium ester labeled binding conjugate; allowing said solid phase, tracer and sample to react to form a reaction mixture comprising a specific binding complex bound to said solid phase and a free fraction unattached to said solid phase; contacting said reaction mixture with an activating agent to flash said acridinium or benzacridinium ester tracer and provide a modulated chemiluminescent signal; measuring said modulated signal; and associating said modulated signal with a reference to determine the amount or presence of said analyte in said sample.

Also provided with this invention is a diagnostic kit for carrying out the above-described method.

Disadvantages inherent in heterogeneous assays employing multiple separations may be avoided using this non-separation method. Additionally, the automation of the assays is easier when the separation step of the assay may be eliminated or less involved, as is accomplished by this invention.

DESCRIPTION OF DRAWINGS

In the Figures included herewith.

DETAILED DESCRIPTION

Figure 1:
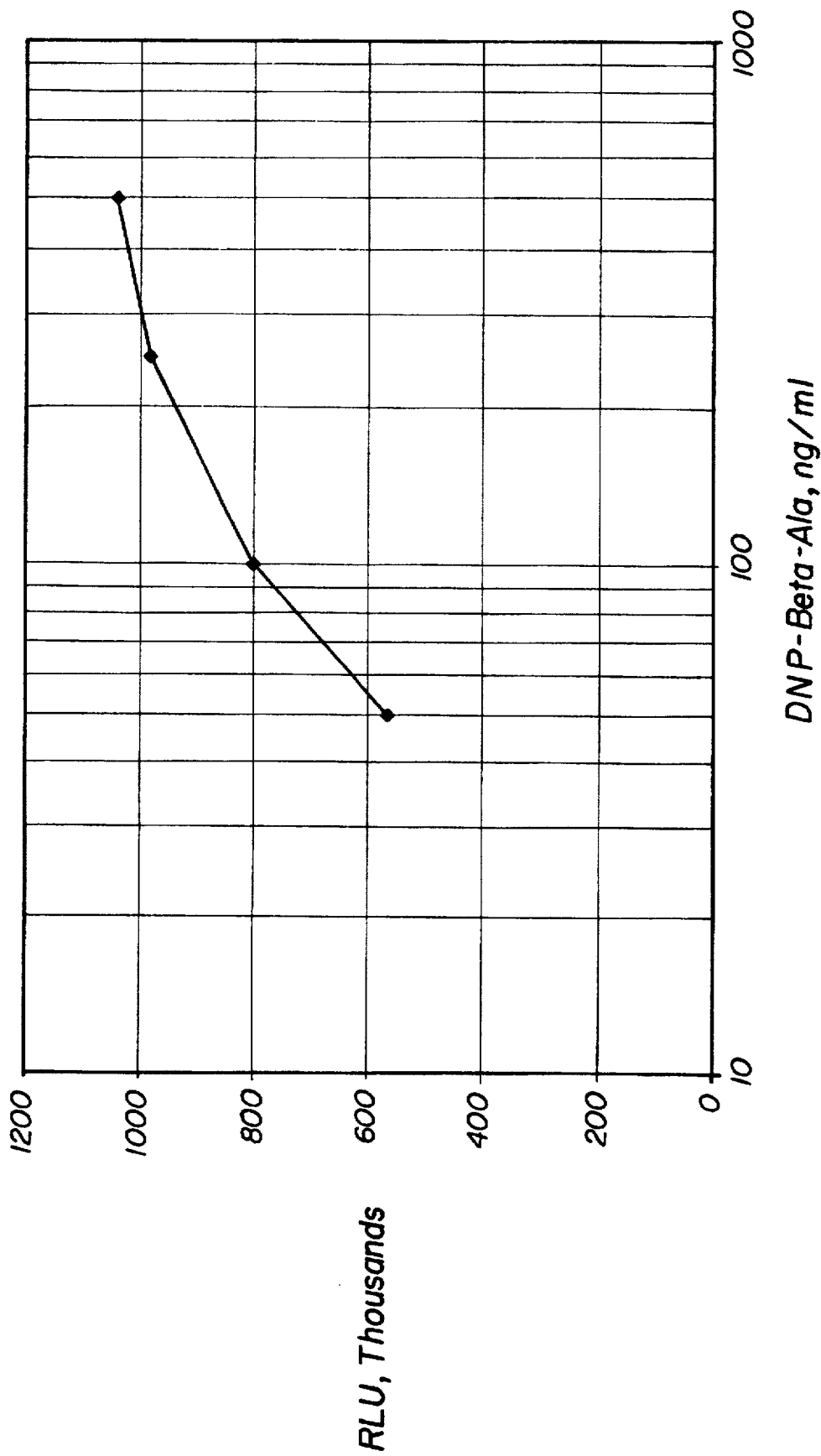
FIG. 1 is a graphical representation of TABLE 1 of Example 2.

The present invention may be employed in detecting and/or quantifying targeted analytes present in chemical or biological substances. Generally any analyte interaction that is stable under chemiluminescence activation conditions may be prepared in this assay system.

Although various types of chemiluminescent compounds having an acridinium, benzacridinium, or acridan type of heterocyclic ring systems are preferred labels, use of equivalent chemiluminescent compounds and means for activating the labels do not depart from the scope of this invention.

Acridinium and benzacridinium esters are currently the more preferred chemiluminescent compounds, with preferred acridinium esters including those compounds having heterocyclic rings or ring systems that contain the heteroatom in a positive oxidation state including such ring systems as acridinium, benz[a]acridinium, benz[b]acridinium, benz [c]acridinium, a benzimidazole cation, quinolinium, isoquinolinium, quinolizinium, a cyclic substituted quinolinium, phenanthridinium, and quinoxalinium, as are well-known in the art. The tracer may be prepared by attaching the selected binding conjugate either directly or indirectly with a reactive functional group present on the acridinium or benzacridinium ester, as is well known to those skilled in the art, e.g. Weeks et al., *Clinical Chemistry*, 29(8), 1474–1479, 1983. Particularly preferred compounds are acridinium and benzacridinium esters with an aryl ring leaving group and the reactive functional group present in either the para or the meta position of the aryl ring. Particularly stable acridinium and benzacridinium esters are those having an aryl ring leaving group, with the aryl ring having an electron donating species (preferably $C_1$–$C_4$ alkyl or alkoxy group, most preferably methyl) present in both ortho positions of the aryl ring and having the reactive functional group (preferably a —COOH which is converted to a N-succinimidyloxycarbonyl group prior to the attachment of the binding partner) in the meta or para position (most preferably para), as described in U.S. Pat. No. 4,745,181 and WO 94/21823, both of which are incorporated by reference.

The solid phase is preferably a metal oxide material preferably chromium oxide, iron oxide, nickel oxide, or any mixture thereof. The solid phase should be water insoluble and maintain structural integrity when exposed to water or biological fluids and may be particulate in nature (varying from a finely divided material, such as that in a magnetic ferrofluid, to a coarse granular material), or a shaped article (such as beads, test tube trays, microtiter plate, membrane, film, filter paper, discs, and so on). More preferably the solid phase particles comprise a core of iron oxide as described in U.S. Pat. No. 4,554,088, issued to Whitehead, et al., 1985 (hereby incorporated by reference). To assist in the attachment of the binding conjugate, preferably the metal oxide solid phase has present a bioaffinity substance present thereon. Silane polymeric coatings are particularly preferred bioaffinity substances and generally may be defined as organofunctional and silicon-functional compounds that are characterized in that the silicon portion of the molecule has an affinity for inorganic materials while the organic portion of the molecule is tailored to combine with organics. Preferably chemical reactions to attach the binding conjugate to the solid phase include, but are not limited to, diazotization, carbodiimide and glutaraldehyde couplings. Coupling techniques that may be used are described in *Method of Enzy.*, 70, p. 159–165 (1980), and Groman, E. V., et al. in *Bio Techniques*, Vol. 3, pp. 156 (1985), and U.S. Pat. No. 4,672,040, issued to Josephson in 1987 (each of which are hereby incorporated by reference).

If the present invention is practiced with gene probes, nucleic acid hybridization may be accomplished using the metal oxide solid phase where the hybridizations are carried out by dispersing a nucleic acid-coupled solid phase (most preferably a DNA oligomer) in a reaction mixture containing molecules to be isolated, allowing the nucleic acid-coupled solid phase to hybridize to a complementary target sequence.

Chemiluminescent light emission of the acridinium ester compounds may be triggered by known activating reagents, typically a base and $H_2O_2$ (including $H_2O_2$ producing compounds) or $O_2$ present in a solvent(s) including water, ethers, esters, alcohols, and ketones, and mixtures thereof. According to the invention, the activating reagent(s) is contacted with the entire reaction mixture after the binding reaction has occurred (i.e. the specific binding complex bound to the solid phase is not separated from the free fraction). Preferably, the activating agent is actually two separate reagents as described below as the "first" reagent (added first to the reaction mixture) and the "second" reagent (added to the reaction mixture promptly after the first reagent). The first reagent is an aqueous acidic hydrogen peroxide solution and the second reagent is a basic aqueous reagent and the chemiluminescent light is measured promptly ("promptly" defined herein as a time period not to exceed several minutes, more preferably less than one minute, most preferably about 0.1 second or so after the second reagent is added to the reaction mixture). The acid of the first reagent may be any suitable acid including nitric acid, hydrochloric acid, sulfuric acid, and mixtures thereof, and the like. Most preferably the acid in the first reagent is nitric acid present in a concentration from about 0.05N to about 0.5N (most preferably about 0.1N) in an aqueous solution having from about 0.1% to about 10% (v/v) hydrogen peroxide present, said % based on the total volume of aqueous solution. The base present in the second reagent is any suitable base, including sodium hydroxide, potassium hydroxide, lithium hydroxide, and mixtures thereof, and the like. Generally, sodium hydroxide is preferred as the base in the second reagent, and may be used in a concentration level of from about 0.25N to about 1.25 N, (most preferably about 0.25N). Additionally, the usual constituents known to those skilled in the art may be included in the activating reagent (s), such as, buffer substances (including phosphate buffer, citrate buffer, borate buffer, and so on), various surfactants and/or preservatives (such as described in U.S. Pat. No. 4,927,769 and pending U.S. Pat. No. 08/339,870, filed Nov. 14, 1994, both commonly assigned to Ciba Corning Diagnostics Corp.), and proteins (including bovine serum albumin, gelatin, casein, and so on). The most preferred activating reagents are: First reagent: aqueous solution of nitric acid (preferably 0.1N) in from about 0.1% to about 10% (preferably from 0.5% to 1%) of hydrogen peroxide; and Second reagent: aqueous solution of from about 0.25N to about 1.25N of NaOH (preferably 0.25N) in water containing from about 0.1 to about 1% (v/v) surfactant (most preferably N-alkyl trimethyl ammonium chloride), with said % based on the total volume of the aqueous reagent solution.

As used herein, the modulated chemiluminescent signal is inclusive of the total chemiluminescent signal provided by the reaction mixture. This includes the quenched chemiluminescent signal provided by tracer bound to the solid phase as well as any tracer that is left in the free fraction solution once the specific binding reaction on the solid phase has transpired. The percent quenching of the chemiluminescent signal is calculated by the following equation:

$$\% \text{ Quench} = \left( 1 - \frac{\text{Modulated Signal Counts}}{\text{Unquenched Signal Counts}} \right) \times 100\%$$

The unquenched signal counts are the counts measured from the chemiluminescent flash of a given amount of the unbound tracer taken in the absence of solid phase. The given amount is defined as the same quantity of tracer as is added to the assay. The % quench calculation may then be associated with a reference (including, for example, a synthetic target sequence DNA and so on) to determine the amount or presence of the analyte in the sample. It has been observed that chemiluminescence is quenched in proportion to the mass of solid phase present during flashing when the solid phase is coated with an irrelevant binding partner. The signal modulation described here is in addition to and of greater magnitude than quenching due to solid phase mass, and is due to the specific binding reaction of the acridinium ester labeled analyte and the binding partner covalently attached to the solid phase.

The evaluation and measurement of the light emission generated by the activation (e.g. flashing) of the chemiluminescent label in all embodiments may be accomplished by techniques known to those skilled in the art. For example, luminometer instruments that may be utilized in measuring the chemiluminescence signals are commercially available, such as the MAGIC® LITE Analyzer (MLA I) instrument manufactured by Ciba Corning Diagnostic Corp., Medfield, Mass. The assay may also be prepared for usage in an automated system that includes a luminometer, with one or more photomultiplier tubes, with multiple photomultiplier tubes described in WO 94/22002, priority filed Mar. 19 1993, commonly assigned and hereby incorporated by reference.

The inventive method may be practiced with various assay systems and formats by techniques known to those skilled in the art. Both competitive and non-competitive (e.g. sandwich) assay formats may be practiced with immunological binding, chemical binding, complementary binding, and combinations thereof.

According to the invention, the following are illustrative of immunological formats that may be used.

Labeled Antigen-Competitive: In this format, the sample containing the targeted antigen to be measured is incubated with a solution comprising (1) a limited amount of antibody coupled to metal oxide solid phase and (2) a tracer comprising an antigen or antigen analogue having attached thereto an acridinium ester label. During an incubation of the reaction solution, the antigen in the sample competes with the labeled antigen (or antigen analogue) for binding to the antibody attached to the solid phase. After the incubation period there may be up to three components left in the reaction solution: (1) a complex comprising the sample antigen bound with the antibody attached to the solid phase (yielding no signal upon activation); (2) a complex comprising the tracer antigen (or antigen analogue) bound with the antibody attached to the solid phase (yielding a quenched signal upon activation); and, possibly, (3) unreacted tracer (yielding an unquenched signal). The amount of labeled antigen (or antigen analogue) bound to the solid phase is inversely proportional to the amount of antigen in the sample.

Labeled Antibody-Competitive: In this format, the sample containing the targeted antigen to be measured is incubated with a solution comprising: (1) a limited amount of antigen (or antigen analogue) coupled to metal oxide solid phase and (2) a tracer comprising an antibody having attached thereto an acridinium ester label. During an incubation of the reaction solution, the antigen in the sample competes with the solid phase antigen (or antigen analogue) for binding to the tracer antibody. After the incubation period there may be up to three components left in the reaction solution: (1) a complex comprising the sample antigen bound with the tracer antibody (yielding an unquenched signal upon activation); (2) a complex comprising the tracer antibody bound with the antigen (or antigen analogue) attached to the solid phase (yielding a quenched signal upon activation); and, possibly, (3) unreacted tracer antibody (yielding an unquenched signal). The antigen in the sample and the antigen (or analogue) on the solid phase compete for the labeled antibody. The amount of labeled antibody that becomes bound to the solid phase is inversely proportional to the amount of antigen there is in the sample.

Labeled Antibody-Sandwich: In this format, which is typically done on antigens which are large enough to bind two antibodies (the same or different) simultaneously, the sample is incubated with an excess of one antibody attached to solid phase together with an excess of another tracer antibody that is labeled with an acridinium ester. The antigen becomes attached to the solid phase via one of its antigenic determinants, and the labeled antibody in turn becomes bound to the antigen via a different determinant. The complex formed on the solid phase (i.e. solid phase antibody-antigen-tracer antibody) yields a quenched chemiluminescent signal upon activation and the unreacted tracer yields an unquenched signal. The amount of labeled antibody that becomes bound to the solid phase is directly proportional to the amount of antigen in the sample.

With regard to hybridization assays (e.g. gene probe assays), the competitive and sandwich formats may be practiced. When employed with hybridization assays, the inventive assay may take advantage of solid phase already present in the assay from the initial hybridization-capture step. For the hybridization quenching phenomenon to be utilized for an assay for specific nucleic sequences, preferably the quenching effect is modulated by partitioning of the labeled oligomer probe between the immobilized and solution phase sequences. In the competitive format, the immobilized oligomer and target sequence therefore preferably share a substantially common sequence that is capable of hybridizing to at least a portion of the labeled oligomer probe.

When practicing the invention in gene probe assays, the acridinium ester may be placed on any desired position of the oligomer, but most preferably the label is placed at the 5' terminus of the molecule. The gene probe assays preferably incorporate an amplification step utilizing a DNA or RNA replicase to generate DNA or RNA copies for each target nucleic acid sequence in the sample by techniques well known to those skilled in the art, such as for example, those described in EP-A-0 481 704 (commonly assigned and incorporated herein by reference). After or during this amplification step, an acridinium ester labeled oligomer is added to the sample. The polynucleotide sequence permits it to hybridize specifically to a portion of the sequence which is being amplified as well as the same sequence immobilized to a metal oxide solid phase which has been added earlier in the assay procedure. The amount of labeled oligomer that will be captured upon the solid phase will depend upon the relative amounts of the complementary sequence present in solution or immobilized on the solid phase. The amount of amplified target sequence produced from the replicase reaction is expected to be in excess over that immobilized upon the solid phase. Using the non-separation chemiluminescent detection method, samples containing no or lower than a threshold amount of target will result in a quench of the light emission of the labeled oligomer while for samples containing targets, the chemiluminescence of the labeled oligomer will remain unquenched. The percent quenching of the labeled oligomer chemiluminescence that occurs upon hybridization to an oligomer attached to the solid phase may be calculated by the following formula:

$$\% Q = \frac{RLU \text{ of reaction containing oligomer- solid phase}}{RLU \text{ of minus oligomer- solid phase control}} \times 100$$

where Q represents quenching and RLU represents Relative Light Units. As shown in the calculation, the hybridization reaction and control reaction are preferably incubated under substantially the same conditions, as the chemiluminescence of the labeled oligomer may generally vary with time, temperature, and buffer conditions.

According to the invention, hybridization of the labeled oligomer to the oligomer attached to the solid phase will result in maximum reduction of the chemiluminescent signal when the solid phase capacity is in excess of the input labeled oligomer. Additionally, an excess labeled oligomer relative to the solid phase will result in less quenching (i.e. excess labeled oligomer that is not hybridized will be detected with higher efficiency by generating more chemiluminescence relative to the control).

The invention may be practiced using complementary substances attached to the tracer and solid phase conjugate. Preferred complementary substances include biotin and avidin. Exemplary biotin compounds include, for example, biocytin (i.e. biotine-N-lysine), biocytin hydrazide, amine or sulfhydryl derivatives of 2-imminobiotin and biotinyl-ε-aminocaprioic acid hydrazide and derivatives of biotin, including, for example, biotin-N-hydroxysuccinimide ester, biotinyl-ε-aminocaprioic acid-N-hydroxysuccinimide ester, sulfosuccinimidyl 6-(biotin amido)-bromoacetylhydrazide, p-diazobenzoyl biocytin and 3-(N-maleimidopropoionyl) biocytin, which can be attached to linking proteins (preferably attached to the solid phase polymeric coating), as is well known to those skilled in the art. Avidin compounds that may be used include streptavidin, succinylated avidin, monomeric avidin, and so on. The method of attaching the avidin and biotin (or derivative of either) either directly or indirectly to the specified tracer or solid phase conjugate may be accomplished through techniques known to those skilled in the art, e.g. through reacting the amino or sulfhydryl groups of the avidin or biotin.

With regard to immunological assays, the invention is particularly useful for detecting or quantifying theophylline and dinitrophenol (DNP) protein and derivatives thereof. With regard to hybridization assays, the invention is particularly effective in detecting or quantifying enteric pathogens, such as, for example, Salmonella and Campylobacter species.

It is to be understood that various modifications to the invention will be apparent to and can readily be made by those skilled in the art, given the disclosure herein, without departing from the scope and materials of this invention. It is noted that the following examples given herein are intended to illustrate and not to limit the invention thereto.

EXAMPLES

The solid phase in all examples consisted of paramagnetic particles (PMP) having a silane polymeric coating around the iron oxide core (purchased from Advanced Magnetics Inc., Cambridge, Mass). The PMP were activated by glutaraldehyde and conjugated with the various specific binding partners according to the two-step procedure as described by Groman, E. V., et al. (*Bio Techniques*, 70, p. 159–165). The acridinium ester (AE) used in the examples was of the following structure:

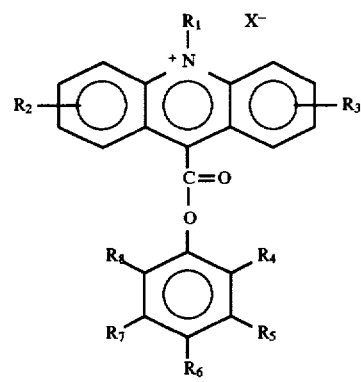

wherein X is $CH_3SO_4$, $R_1$ is methyl; $R_2$, $R_3$, $R_5$ and $R_7$ are hydrogen; $R_4$ and $R_8$ are methyl, $R_6$=is an COOH converted to a N-succinimidyloxycarbonyl group to assist in attachment of a specific binding partner. A description of a technique that was used in attaching acridinium esters with binding conjugates is as found in Weeks et al., *Clinical Chemistry*, 29(8), 1474–1479 (1983) and EP-A-0 537 994 (each of which are hereby incorporated by reference). The assays were flashed with two reagents, as follows: Flash Reagent 1=about 0.3 ml of 0.1N $HNO_3$ in approx. 0.5% aqueous solution of $H_2O_2$. Flash Reagent 2=about 0.3 ml of 0.25N NaOH in a approx. 0.5% aqueous solution of ARQUAD® 16–50N-alkyl trimethyl ammonium chloride (50% active purchased from AKZO Chemical Inc., Chicago, Ill.). Flash Reagent 1 was added to the reaction mixture first, followed immediately with Flash Reagent 2. Relative light units (RLU's) were measured over a 2 second interval after injection of Flash Reagents 1 and 2 using a luminometer (MAGIC® Lite Analyzer "MLA I", Ciba Corning Diagnostics Corp., Medfield, Mass.).

The % Quench was calculated by the following equation:

$$\% \text{ Quench} = \left(1 - \frac{\text{Modulated Signal Counts}}{\text{Unquenched Signal Counts}}\right) \times 100\%$$

The modulated signal counts were a measurement of the total signal provided by the reaction mixture after the reaction between specific binding partners transpired. The unquenched signal counts were a measurement of the light emitted from an amount of tracer added to the assay, as flashed in the absence of solid phase.

Example 1

This example demonstrates the antibody-dependent quenching phenomenon.

Monoclonal antibodies to 2,4-dinitrophenol(DNP) were prepared by standard methods, after immunizing mice with a conjugate of DNP with thyroglobulin (DNP-TG). This conjugate was prepared by reaction of equal weights of thyroglobulin and 2,4-dinitrobenzenesulfonic acid in 0.15M $Na_2CO_3$ solution for 18 hours, followed by exhaustive dialysis against 0.001M sodium phosphate buffer, pH 7.4.

The antibody (anti-DNP) was purified from ascites fluid by precipitation of unwanted protein with caprylic acid, followed by dialysis of the supernatant against 0.1M sodium phosphate buffer, pH 7.4.

For immobilization of the antibody, 10 mg of PMP were activated with 6.25% glutaraldehyde in 0.1M phosphate, pH 7.4, for 2 hours. After washing to remove excess glutaraldehyde, the PMP were mixed with 1 ml of a solution of antibody (diluted to 1.5 mg/ml), and let stand overnight. The particles were then washed several times in phosphate buffer, and finally resuspended to a concentration of 10 mg/ml in 0.05M sodium phosphate, pH 7.4, 0.15M NaCl, 1 mg/ml bovine serum albumin (PBS/BSA).

DNP-TG (prepared as above) and a conjugate of fluorescein isothiocyanate with bovine serum albumin (FITC-BSA) (purchased from Sigma Chemical Co., St. Louis, Mo.) were labeled with the acridinium ester (AE) as follows: 2 mg of conjugate in 1 ml of 0.1M sodium phosphate, 0.15M NaCl, pH 8.0, was mixed with 80 µl of AE (1 mg/ml in dimethylformamide) and incubated for 1 hr at room temp. The mixture was then added to 0.5 ml of a 10 mg/ml solution of DL-lysine and incubated for 15 minutes. The labeled conjugate was then purified by gel filtration on a 20 cm column of Sephadex G 25.

DNP-β-alanine was prepared as follow: One gram of β-alanine was dissolved in 50 ml of 1M $NaHCO_3$. Seven milliliters of 2,4-dinitrofluorobenzene (DNFB) was added to 100 ml of ethanol, and this was added to the β-alanine and stirred at room temperature for two hours. The ethanol was removed by rotary evaporation and the remainder extracted with ether to remove excess DNFB. Normal HCl was added to the aqueous part until a precipitate formed. The latter was recovered by filtration, washed with ether, and air dried. The material was recrystallized twice: first from water with the addition of 1N HCl, then from $NaHCO_3/Na_2CO_3$, pH=9, washed with ether, and dried.

One hundred microliters of the anti-DNP PMP (diluted 1:30 with PBS/BSA) was incubated with either 100 µl of AE-DNP-TG (diluted with 1:15000 with PBA/BSA) or with 100 µl of AE-FITC-BSA (diluted 1:60000 with PBA/BSA). After one hour, the chemiluminescent light emission of each mixture was measured and compared to that of the same amount of each AE-labeled conjugate in the absence of the anti-DNP PMP. For the AE-DNP-TG conjugate, 52% of the light output was quenched by the particles carrying the specific anti-DNP antibody. For the AE-FITC-BSA conjugate, which is not bound by this antibody, only 26% of the light was quenched by the particles.

These data support that quenching is increased upon the formation of the specific binding reaction complex on the solid phase. These findings are contrary to the expectation that the amount of quenching of light emission from a given amount of labeled tracer by a given mass of solid phase would be the same.

Example 2

The following example illustrates the effect of addition of a DNP derivative (not labeled with acridinium ester) to the system described in Example 1.

One hundred microliters of anti-DNP-PMP (diluted 1:30 with PBS/BSA) was incubated with 50 µl of AE-DNP-TG (diluted 1:7500 with PBS/BSA) and with 50 µl of a solution of DNP-β-alanine at concentrations of 50 to 500 ng/ml. After one hour, the chemiluminescence of each mixture was measured. The results are shown in TABLE 1 below and graphically represented in FIG. 1.

TABLE 1

| Effect of Addition of a DNP Derivative | |
|---|---|
| DNP-β-Alanine (ng/ml) | Chemiluminescence (RLU) |
| 0 | 545,000 |
| 50 | 566,000 |
| 100 | 802,000 |
| 250 | 983,000 |
| 500 | 1,040,000 |

The data show that addition of increasing concentrations of an unlabeled DNP derivative resulted in a progressive increase in light output. This effect is presumably due to the unlabelled DNP competing for the immobilized antibody's available binding sites, resulting in less of the AE-labeled DNP binding to the particles, and thus diminishing the quenching of chemiluminescent light emission.

Example 3

Monoclonal antibodies to theophylline and lutenizing hormone (LH) were generated by standard techniques after immunization of mice with 8-carboxypropyltheophylline-thyroglobulin and LH respectively. Polyclonal antibody to theophylline was produced by immunization of rabbits with 8-carboxypropyltheophylline-thyroglobulin. Monoclonal and polyclonal antibody (anti-LH) were purified as described above for Examples 1 and 2 except that activation and coupling were done in 0.01M sodium acetate buffer (pH 5.5). Particles were finally resuspended at 25 mg/ml in PBS/BSA buffer. Theophylline standards were prepared by diluting a stock solution of theophylline (Sigma) into PBS/BSA for buffer based standards or drug-free human serum for serum standards. Standards from a Theophylline RIA kit obtained from Clinical Assays were also used.

PMP immobilized with either theophylline monoclonal antibody (THEO) or LH monoclonal antibody was serially diluted from 2.5 mg/ml to 0.156 mg/ml in PBS/BSA buffer. Five hundred microliters of PMP was dispensed to test tubes, the buffer was removed after magnetic separation of the particles and 100 µl of water was added to resuspend the particles. AE-THEO (0.4 million RLU/tube) diluted in PBS/BSA was added to each tube. The chemiluminescent light emission was immediately measured using the MLA I.

The RLU observed for the solution of AE-THEO with the anti-theophylline PMP and the anti-LH PMP (modulated signal total counts) were compared to the RLU measured in the absence of PMP (unquenched total counts). The results are summarized in TABLE 2 as follows.

TABLE 2

| Quenching of AE-Theophylline in the Presence of Anti-Theophylline Antibody PMP (Anti-THEO) and Anti-Luteotropic Hormone Antibody PMP (Anti-LH) | | | |
|---|---|---|---|
| Antibody on PMP | (PMP) mg/tube | RLU | Quench % |
|  | 0 | 335937 (UTC) | 0 |
| Anti-LH | 0.075 | 294570 | 13 |
| Anti-LH | 0.156 | 244583 | 27 |
| Anti-LH | 0.312 | 215243 | 36 |
| Anti-LH | 0.625 | 157693 | 53 |
| Anti-LH | 1.25 | 105153 | 69 |
|  | 0 | 412450 (UTC) | 0 |
| Anti-THEO | 0.075 | 39865 | 90 |
| Anti-THEO | 0.156 | 30915 | 92 |

TABLE 2-continued

Quenching of AE-Theophylline in the Presence of Anti-Theophylline Antibody PMP (Anti-THEO) and Anti-Luteotropic Hormone Antibody PMP (Anti-LH)

| Antibody on PMP | (PMP) mg/tube | RLU | Quench % |
|---|---|---|---|
| Anti-THEO | 0.312 | 24900 | 94 |
| Anti-THEO | 0.625 | 19635 | 95 |
| Anti-THEO | 1.25 | 13255 | 97 |

Figure 2:
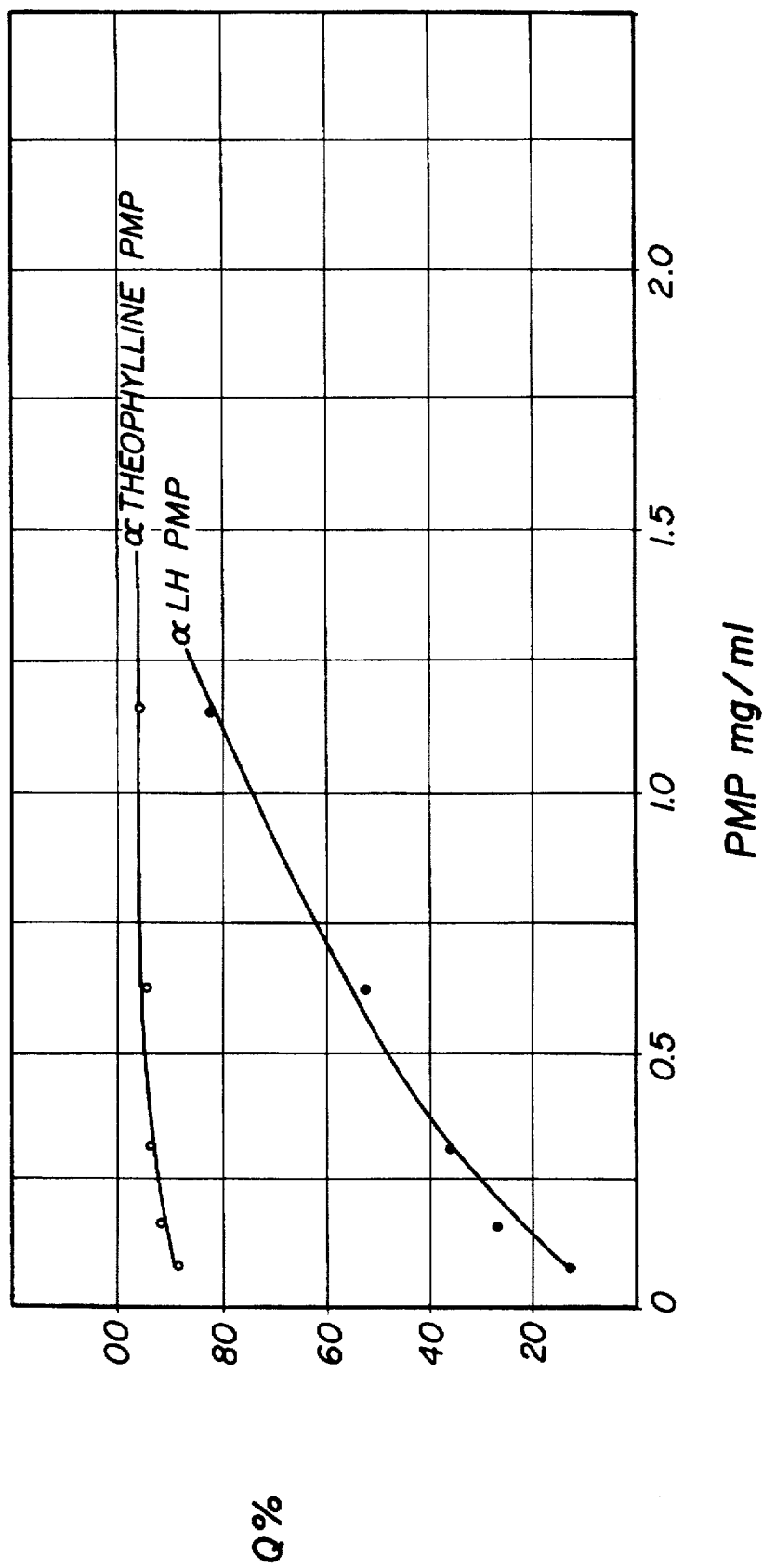
FIG. 2 is a graphical representation of TABLE 2 of Example 3, showing both α-Theophylline PMP and α-LH PMP.

TABLE 2 is graphically represented in FIG. 2, where separate lines represent α-Theophylline PMP and α-LM PMP, as labeled. The data shown in TABLE 2 and FIG. 2 illustrate that the Quench % observed when the anti-THEO PMP was present seemed to be relatively independent of the concentration of PMP mass over this range. In contrast, quenching of counts in relation to the mass of particles was observed when the particles were coupled with an "irrelevant" antibody (anti-LH) was obtained.

Example 4

Patient samples were obtained from an clinical laboratory (Metpath, Inc.). Theophylline levels for patient samples were obtained using a commercially available assay, TDX Theophylline Assay (Abbott Laboratories, Abbott Park, Ill.).

Figure 3:
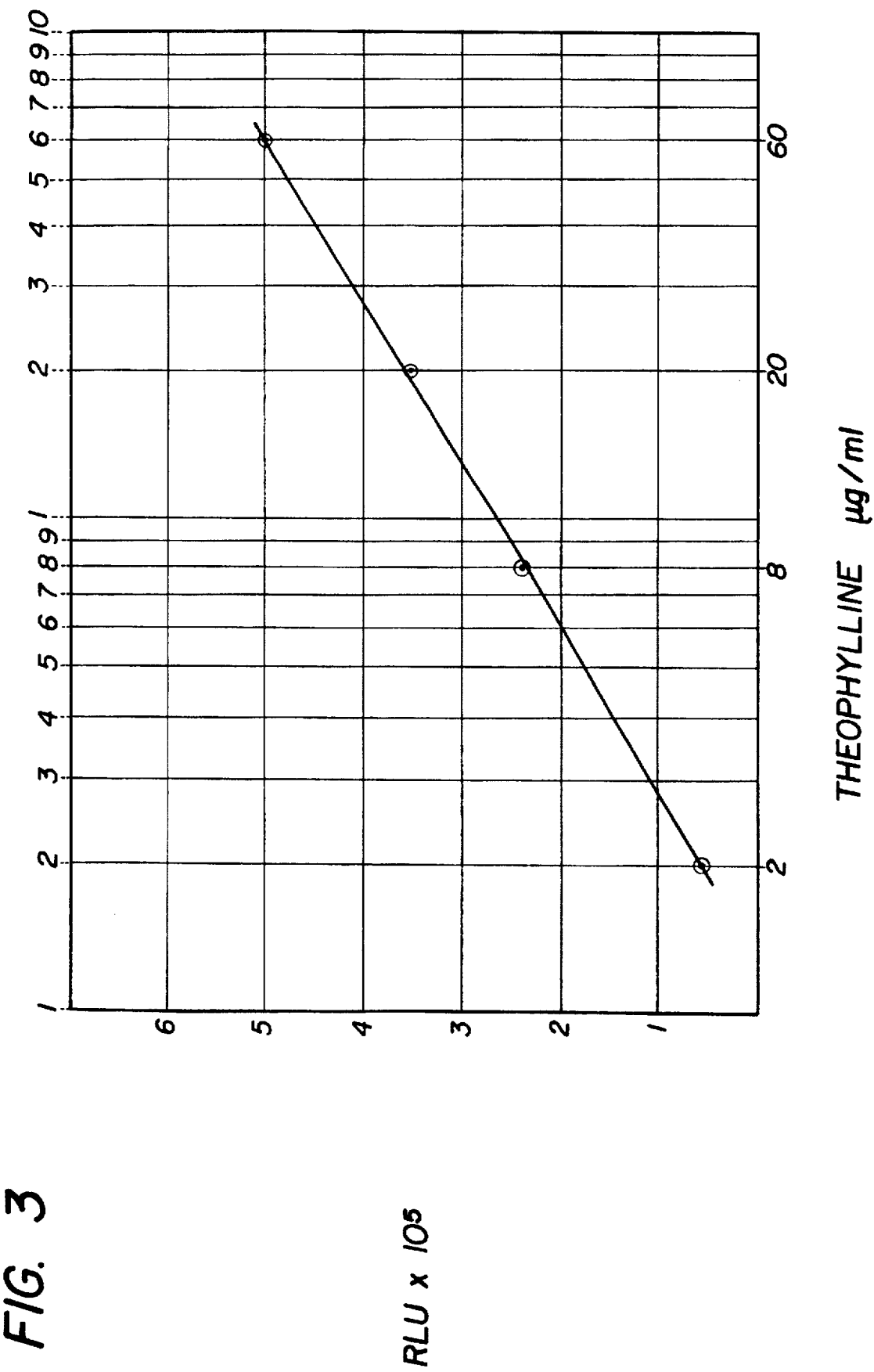
FIG. 3 is a standard curve for the measurement of theophylline, as used as a reference in Example 4.

Non-separation theophylline assays were run as follows. Standards, controls or patient samples were incubated with AE-theophylline and monoclonal anti-theophylline PMP at room temperature for 10 minutes. Chemiluminescence was measured in the MLA I without further manipulation of the tubes. At low analyte concentration, most of the tracer was bound to the solid phase and did not flash, thus giving low counts. As the analyte concentration increased, more tracer remained unbound, thus giving a higher signal. A sample standard curve is shown in FIG. 3. The results of an assay of 14 patient samples are given in TABLE 3. A commercially available theophylline assay (TDX assay purchased from Abbott) was used as the control, with the control data shown in TABLE 3.

TABLE 3

NON-SEPARATION THEOPHYLLINE ASSAY

| PATIENT | Theophylline, μg/ml CONTROL TDX (μg/ml) | NON-SEPARATION ASSAY INVENTION (μg/ml) |
|---|---|---|
| 1 | 5.2 | 8.3 |
| 2 | 16.0 | 13.0 |
| 3 | 7.1 | 6.8 |
| 4 | 11.1 | 12.9 |
| 5 | 13.2 | 9.3 |
| 6 | 4.6 | 4.8 |
| 7 | 23.2 | 19.8 |
| 8 | 14.6 | 14.6 |
| 9 | 5.0 | 6.4 |
| 10 | 15.9 | 10.5 |
| 11 | 8.7 | 6.8 |
| 12 | 5.6 | 6.1 |
| 13 | 11.4 | 7.7 |
| 14 | 14.4 | 9.0 |

Correlation:
Non Separation Assay = 2.42 + 0.656 TDX  R = 0.874

Example 5-7

Hybridization Assays

The nucleic acid sequences used in the hybridization assays described in Examples 5-7 are provided in sequence listing herewith, where the following abbreviations are used in presenting the hybridization assays: adenine (A); thymine (T); uracil (U); guanine (G); cytosine (C).

PM979: shown as SEQ. NO. 1, where bases 1–10 constitute a spacer arm, bases 11–46 consist of the 5' sequence of the nanovariant (+) template, and bases 47–70 are complementary to a Salmonella specific target sequence.

MASA5: shown as SEQ. NO. 2, where bases 1–10 constitute a spacer arm, bases 11–71 consist of the 5' sequence of the midivariant (+) template, and bases 72–95 are complementary to a Salmonella specific target sequence.

PM1076: shown as SEQ. NO. 3, where half of the Salmonella target, complementary to PM979 and MASA5 was employed.

PM2058: shown as SEQ. NO. 4, where the Salmonella target, complementary to PM979 and MASA5 was employed. Some versions of this sequence have a 5'-amino group for conjugation with acridinium ester, as described herein.

SA7: anti-Salmonella target, shown as SEQ. No. 5.

MD24: shown as SEQ. NO. 6, where a probe complementary to bases 34–57 of the midivariant (+) template; i.e. bases 44–67 of MASA5 was used. Some versions of this sequence have a 5'amino group for conjugation with acridinium ester, as described herein.

MDV-SA2 RNA Transcript: shown as SEQ. NO. 7, where bases 1–61 consist of the 5' end of the midivariant (+) template, bases 62–69 and 118–123 are plasmid linker sequences, bases 70–117 are complementary to a Salmonella specific target sequence, and bases 124–282 consist of the 3' end of the midivariant (+) template.

The solid phases consisted of PMP to which one of the amplification oligomer probes was covalently attached (via a 5'-terminal amino group using a hetero-bifunctional coupling reagent for PM979, or by glutaraldehyde activation of the PMP for MASA5). The AE-PM1076 and 5' $^{32}$P-PM2058 sequences are complementary to the anti-target portion of the immobilized probes (therefore hybridization and capture occur simultaneously). The PM979-PMP was prepared using PM 979 oligomer (obtained from Promega Corp., Madison, Wis.) and a thio-terminated PMP (purchased from Advanced Magnetics, Cambridge, Mass). The AE labeled PM1076 (AE-oligomer) was prepared using the dimethyl acridinium ester label and PM1076 oligomer obtained from Promega Corp. The MASA5-PMP was prepared using MASA5 oligomer (obtained from Promega Corp.) and a thio-terminated PMP purchased from Advanced Magnetics. The PM 2058 oligomer was also obtained from Promega Corp. The sodium citrate was purchased from Mallinckrodt, Inc., St. Louis, Mo. The NaCl, Tris EDTA and Tween-20 were all purchased from Sigma Chemical, Co., St. Louis, Mo.) and the BSA (Fraction V) from Miles, Inc.

Example 5

This example illustrates the quenching of AE-oligomer chemiluminescence by hybridization to oligomer-PMP.

Hybridization reactions containing PM979 immobilized on PMP (PM979-PMP) and AE-PM1076 (AE-oligomer) were set up on ice by adding 40 μl of 60 mM sodium citrate, 600 mM sodium chloride, 10 mM tris-(hydroxymethyl) aminomethane (Tris) HCl, 1 mM ethylene diaminetetraacetic acid (EDTA), 0.1% (w/v) BSA, and 0.02% (v/v) polyoxyethylene (20) sorbitan monolaurate (TWEEN-20) at pH 7.5 (hereinafter "buffer") to ten tubes. Secondly, 5 μl of buffer containing 50 μg of PM979-PMP was added to five of the ten tubes, and 5 μl of buffer alone was added to the remaining five tubes for control reactions. Finally, 5 μl of buffer containing 10, 32, 100, 320, and 1000 femtomoles (1 fmol=1×10$^{-15}$ moles) of AE-PM1076 was added to pairs of tubes, one group containing PMP and one control group without PMP (control for AE decomposition during hybridization). All reactions were incubated at 56° C. and 5 μl samples were removed at 0, 75, 120, and 180 minutes, added to 100 μl of water, flashed with Reagents 1 and 2 in a luminometer to determine the chemiluminescent activity.

Figure 4:
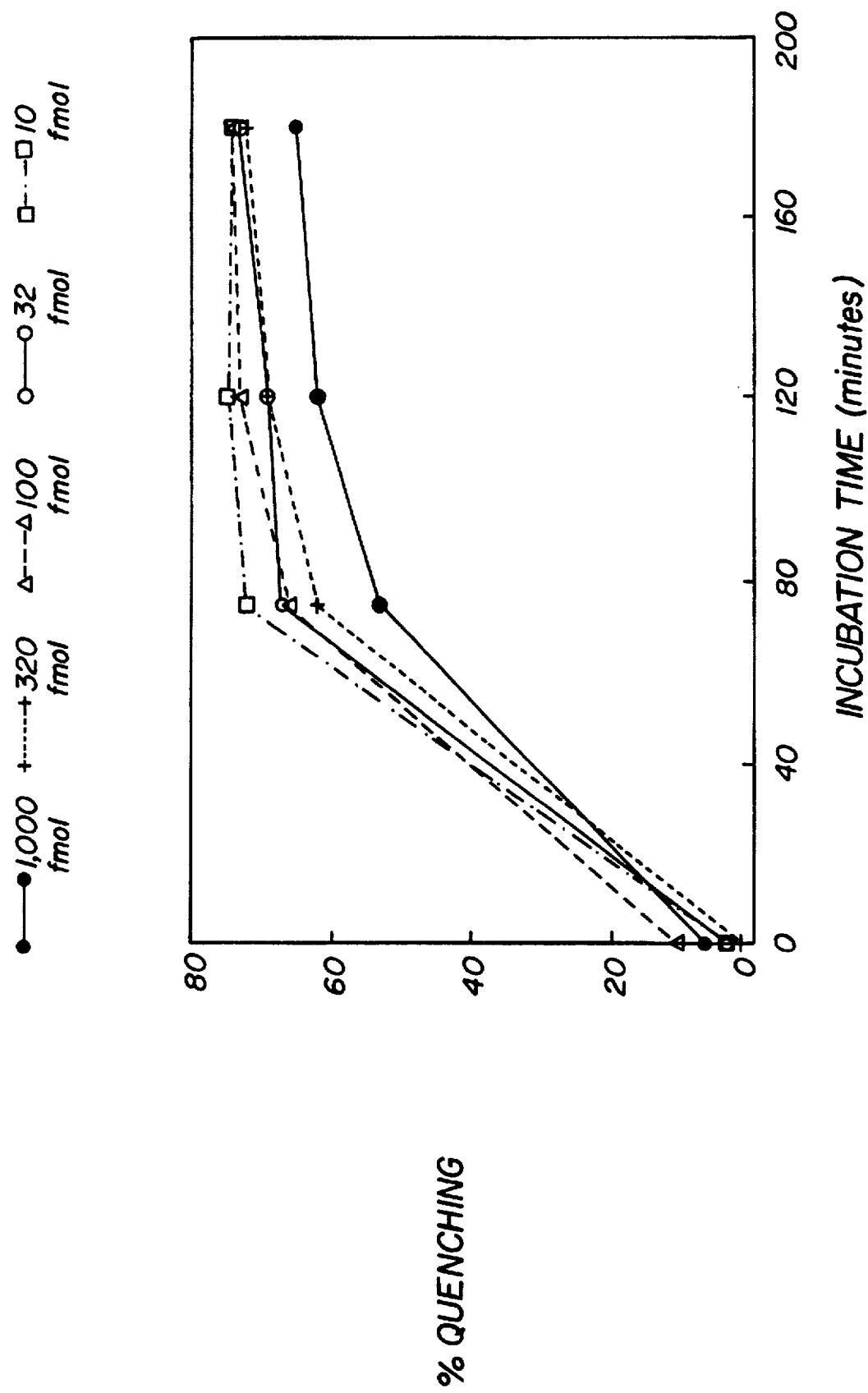
FIG. 4 is described in Example 5.

The % Quench was calculated from the signals measured from the various tubes and are presented in FIG. 4. As shown in FIG. 4, the chemiluminescence of all reactions containing oligomer-PMP decreased dramatically relative to the corresponding control without oligomer-PMP, up to a maximum of 74%, upon hybridization. Also the data demonstrate conditions where the relative input of AE-oligomer and oligomer-PMP generated significant quenching. The conditions of the reaction having 100 fmol input of the AE-oligomer, where the solid phase capacity is five-times the input of AE-oligomer, were chosen to test the feasibility of the competitive assay of Example 6.

Example 6

Figure 5:
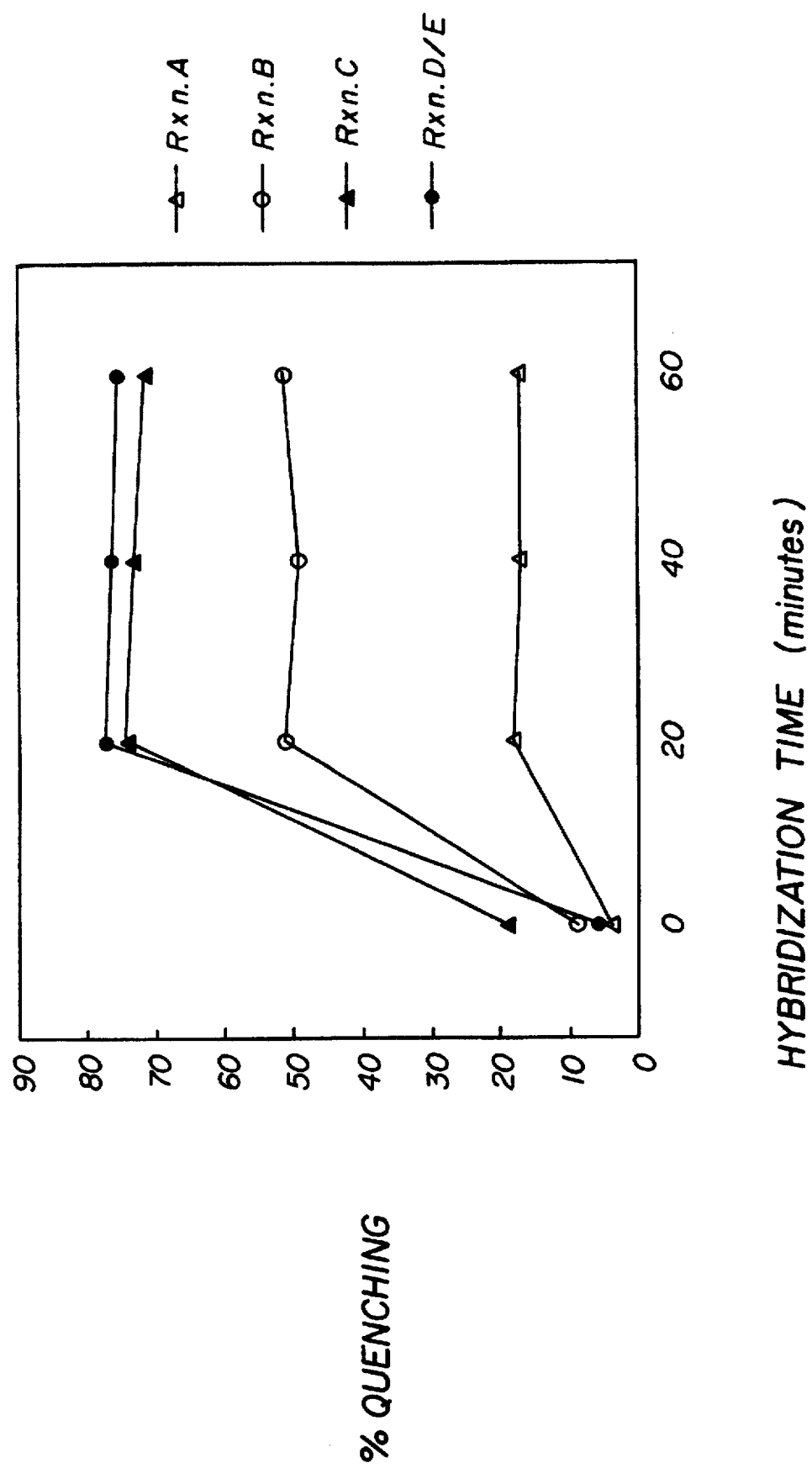
FIG. 5 illustrates a competition hybridization assay as described in Example 6.

Hybridization reactions were set up on ice by adding 10 μl of buffer (described in Example 5) alone or 10 μl of buffer containing 100 μg of PM979-PMP to each of five tubes. Next, 10 μl of buffer containing 0, 10$^{-14}$, 10$^{-13}$, 10$^{-12}$, and 10$^{-11}$ moles of standard, PM979 (the oligomer that was immobilized on the PMP), was added to one of the tubes containing PM979-PMP and one control tube without PMP for each amount of added standard. Finally, 80 μL of buffer containing 200 fmol of AE-PM1076 was added to all reactions. All tubes were incubated at 56° C. Duplicate 10 μl samples were removed from each reaction at the indicated times (0, 20, 40, and 60 minutes), added to 100 μl of water and processed in a luminometer to determine chemiluminescent activity. Results are shown in TABLES 4 (FIG. 5) and 5. TABLE 5 shows data derived from the 20 minute data from TABLE 4. The results shown are consistent with theoretical expectations, i.e. the same maximum extent of quenching was achieved in all hybridizations except where the input of PM979 in solution exceeds the solid phase capacity.

TABLE 4

| COMPETITIVE HYBRIDIZATION QUENCHING ASSAY | | | | | |
|---|---|---|---|---|---|
| REACTION | Standard Input[1] (moles) | Hybrid. Time (min) | Total Signal (RLU × 10$^{-5}$) | | Quench %[2] |
| | | | (+)PMP | (−)PMP | |
| A | 10$^{-11}$ | 0 | 8.27 | 8.66 | 4 |
| | | 20 | 4.61 | 5.65 | 18 |
| | | 40 | 4.78 | 5.78 | 17 |
| | | 60 | 4.38 | 5.30 | 17 |
| B | 10$^{-12}$ | 0 | 7.82 | 8.60 | 9 |
| | | 20 | 2.60 | 5.28 | 51 |
| | | 40 | 2.71 | 5.31 | 49 |
| | | 60 | 2.63 | 5.39 | 51 |
| C | 10$^{-13}$ | 0 | 7.62 | 9.36 | 19 |
| | | 20 | 1.43 | 5.43 | 74 |
| | | 40 | 1.48 | 5.56 | 73 |
| | | 60 | 1.51 | 5.21 | 71 |
| D | 10$^{-14}$ | 0 | 8.05 | 8.57 | 6 |
| | | 20 | 1.21 | 5.21 | 77 |
| | | 40 | 1.28 | 5.26 | 76 |
| | | 60 | 1.26 | 5.11 | 75 |

TABLE 4-continued

| COMPETITIVE HYBRIDIZATION QUENCHING ASSAY | | | | | |
|---|---|---|---|---|---|
| REACTION | Standard Input[1] (moles) | Hybrid. Time (min) | Total Signal (RLU × 10$^{-5}$) | | Quench %[2] |
| | | | (+)PMP | (−)PMP | |
| E | 0 | | 8.00 | 8.45 | 5 |
| | | | 1.15 | 5.41 | 79 |
| | | | 1.26 | 5.27 | 76 |
| | | | 1.24 | 4.82 | 74 |

[1] Standard was added PM979.
[2] $[1 - (+PMP\ RLU) \div (-PMP\ RLU)] \times 100\% = \%$ Quenching

TABLE 5

| COMPETITIVE HYBRIDIZATION QUENCHING ASSAY -20 minute data point- | | | |
|---|---|---|---|
| Reaction | Standard Input (moles) | (+)PMP Signal (RLU)[1] | Net (+)PMP Signal (RLU)[2] |
| A | 10$^{-11}$ | 461,480 | 346,830 |
| B | 10$^{-12}$ | 259,560 | 144,910 |
| C | 10$^{-13}$ | 142,860 | 28,210 |
| D | 10$^{-14}$ | 120,720 | 6,070 |
| E | 0 | 114,650 | 0 |

[1] Derived from the 20 minute data point of TABLE 4.
[2] (+PMP RLU)$_i$ ÷ (+PMP RLU)$_E$.
i = "+PMP RLU" value
E = "Reaction E" value As shown by the data above, this example demonstrates a hybridization competition assay for synthetic DNA oligomer. Varying amounts of the same oligomer that had been immobilized on the PMP were added in solution to compete with the solid phase immobilized oligomer for hybridization of the AE-oligomer, i.e. the added oligomer functioned as a competitive standard. This mimics the competition that would take place due to the presence of amplified probe in the proposed assay of Example 7.

Example 7

Amplification reactions that had started with 0, 10$^{-16}$, 10$^{-18}$, 10$^{-19}$, and 10$^{-20}$ moles of midivariant template, respectively, were terminated by addition of EDTA and put on ice.

Hybridization reactions were set up on ice by adding 5, 20, 70, or 75 μl of buffer to 12 tubes, so that the final volume would be 100 μl after addition of all other components, as described above. Next 50 μl of buffer containing 5 of PM979-PMP was added to six tubes. Then 5 μl of buffer or one of the five replication reactions was added to pairs of tubes, one with and one without PMP. Finally, 25 μl of buffer containing 10 fmol of AE-MD24 was added to all tubes. All tubes were incubated for 20 minutes at 56° C. then flashed with Reagents 1 and 2 in a luminometer to determine the chemiluminescent activity.

The results, shown in Table 6, do not reflect the presence of abundant replicated midivariant RNA (estimated to be on the order of 5 pmol per reaction). The failure of the assay to detect the presence of midivariant sequence was not due to reagent quality, since reagents had been validated by titration and mock assays with synthetic target. Additional trials, with heat denaturation of the target prior to addition and increased input of AE-oligomer, also failed. Subsequent experiments using $^{32}$P-labeled MD24 suggest that the failure is due to inefficient hybridization of the probe to the target, presumably due to higher stability of a midivariant duplex.

This hypothesis is supported by the results of a quench assay for transcribed single stranded midivariant target, which produced a standard curve with quench values consistent with theoretical expectations with respect to the molar ratio of target and AE-probe.

TABLE 6

HYBRIDIZATION QUENCH ASSAY
FOR REPLICATION PRODUCTS

| Reaction | Added Template (mol) | +PMP or −PMP | Mean RLU | % Quench[1.] |
|---|---|---|---|---|
| A | buffer only | − | 235,545 | 70 |
|   |   | + | 71,325 |   |
| B | 0 (mock reaction) | − | 190,240 | 65 |
|   |   | + | 66,690 |   |

TABLE 6-continued

HYBRIDIZATION QUENCH ASSAY
FOR REPLICATION PRODUCTS

| Reaction | Added Template (mol) | +PMP or −PMP | Mean RLU | % Quench[1.] |
|---|---|---|---|---|
| C | $10^{-16}$ | − | 190,055 | 65 |
|   |   | + | 66,570 |   |
| D | $10^{-18}$ | − | 189,950 | 64 |
|   |   | + | 67,820 |   |
| E | $10^{-19}$ | − | 178,270 | 64 |
|   |   | + | 63,780 |   |
| F | $10^{-20}$ | − | 164,590 | 63 |
|   |   | + | 60,190 |   |

[1.] % Q = [1 − (+PMP value)/(−PMP value)] × 100

---

That which is claimed is:

1. A non-separation specific binding assay to detect or quantify the presence of an analyte, said assay comprising:
  (a) contacting a sample with a solid phase, which comprises a metal oxide and to which is attached a first binding conjugate, and with a tracer, which comprises an acridinium or benzacridinium ester labeled second binding conjugate, wherein said first and second binding conjugates may be the same or different;
  (b) allowing said solid phase, tracer and sample to react to form a reaction mixture comprising a specific binding complex attached to said solid phase and a free fraction unattached to said solid phase;
  (c) contacting said reaction mixture with an activating agent to flash said acridinium or benzacridinium ester tracer and provide a modulated chemiluminescent signal;
  (d) measuring said modulated signal; and
  (e) associating said modulated signal with a reference to determine the amount or presence of said analyte in said sample;
    wherein said modulated signal is the total chemiluminescent signal from the reaction mixture including the quenched chemiluminescent signal contributed by the tracer that is bound to the solid phase and the chemiluminescent signal from any tracer remaining in said free fraction;
    wherein the amount of tracer of said step (a) is separately activated to emit a chemiluminescent light emission that is measured in the absence of said solid phase resulting in a unquenched signal count measurement;
    wherein a % quench effect is calculated using said modulated signal of said step (d) and the unquenched signal count by an equation:

$$\% \text{Quench} = \left(1 - \frac{\text{Modulated Signal Counts}}{\text{Unquenched Signal Counts}}\right)$$

wherein said % quench effect is associated with said reference of said step (e) to provide a determination of the presence or the amount of said analyte.

2. An assay according to claim 1 wherein said specific binding complex is formed by an immunological reaction.

3. An assay according to claim 2 wherein said metal oxide solid phase comprises iron oxide.

4. An assay according to claim 3 wherein said activating agent comprises a first reagent comprising an aqueous solution of acidic hydrogen peroxide and a second reagent comprising a basic aqueous solution, with said first reagent contacted with said reaction mixture prior to said second reagent.

5. An assay according to claim 4 wherein said first reagent has an acid component selected from the group consisting of nitric acid, hydrochloric acid, sulfuric acid, and mixtures thereof and said second reagent has a base selected from the group consisting of sodium hydroxide, potassium hydroxide, lithium hydroxide and mixtures thereof.

6. An assay according to claim 5 wherein in said first reagent said acid is present in an amount ranging from about 0.1N to about 0.5N in an aqueous solution of hydrogen peroxide present in an amount ranging from about 0.1% to about 10% (v/v), based on the total volume of the aqueous first reagent solution, and in said second reagent said base is present in the aqueous solution in a concentration ranging from about 0.25N to about 1.25N.

7. An assay according to claim 6 wherein said first reagent comprises an aqueous solution of 0.1N nitric acid in from 0.5% to 1% hydrogen peroxide and said second reagent comprises an aqueous solution of 0.25N sodium hydroxide and a surfactant present in an amount ranging from about 0.1% to about 1% (v/v), based on the total volume of the aqueous second reagent.

8. An assay according to claim 7 wherein said analyte is selected from the group consisting of theophylline or a dinitrophenol protein.

9. An assay according to claim 1 wherein said assay is a hybridization assay and said specific binding complex is formed by complementary binding.

10. An assay according to claim 9 wherein said metal oxide solid phase comprises iron oxide.

11. An assay according to claim 10 wherein said activating agent comprises a first reagent comprising an aqueous solution of acidic hydrogen peroxide and a second reagent comprising a basic aqueous solution, with said first reagent contacted with said reaction mixture prior to said second reagent.

12. An assay according to claim 11 wherein said first reagent has an acid component selected from the group consisting of nitric acid, hydrochloric acid, sulfuric acid, and mixtures thereof and said second reagent has a base selected from the group consisting of sodium hydroxide, potassium hydroxide, lithium hydroxide and mixtures thereof.

13. An assay according to claim 12 wherein in said first reagent said acid is present in an amount ranging from about 0.1N to about 0.5N in an aqueous solution of hydrogen peroxide present in an amount ranging from about 0.1% to about 10% (v/v), based on the total volume of the aqueous first reagent solution, and in said second reagent said base is present in the aqueous solution in a concentration ranging from about 0.25N to about 1.25N.

14. An assay according to claim 13 wherein said first reagent comprises an aqueous solution of 0.1N nitric acid in from 0.5% to 1% (v/v) hydrogen peroxide and said second reagent comprises an aqueous solution of 0.25N sodium hydroxide and a surfactant present in an amount ranging from about 0.1% to about 1% (v/v), based on the total volume of the aqueous second reagent.

15. An assay according to claim 1 wherein said binding reaction is immunological and said analyte is selected from the group consisting of theophylline and a dinitrophenol protein.

16. An assay according to claim 1 wherein said binding reaction is complementary binding and said analyte is an enteric pathogen.

17. A non-separation specific binding assay to detect or quantify an analyte in a sample, said assay comprising, in the order stated:

(a) incubating a solution comprising: a sample; a solid phase which comprises a metal oxide and to which is coupled a binding partner specific to said analyte; and a tracer comprising said analyte or analyte analogue having attached thereto an acridinium or benzacridinium ester;

(b) allowing said solution to react to form a reaction mixture comprising a specific binding complex comprising said tracer bound to said solid phase and a free fraction comprising unreacted tracer;

(c) contacting said reaction mixture with a first activating reagent comprising an acidic hydrogen peroxide solution;

(d) contacting said mixture of step (c) with a second activating reagent comprising a basic aqueous solution to provide a modulated chemiluminescent signal;

(e) measuring said modulated chemiluminescent signal; and (f) associating said modulated signal with a reference to determine the amount or presence of said analyte in said sample;

wherein said modulated signal is the total chemiluminescent signal from the reaction mixture including the quenched chemiluminescent signal contributed by the tracer that is bound to the solid phase and the chemiluminescent signal from any tracer remaining in said free fraction;

wherein the amount of tracer of said step (a) is separately activated to emit a chemiluminescent light emission that is measured in the absence of said solid phase resulting in a unquenched signal count measurement;

wherein a % quench effect is calculated using said modulated signal of said step (e) and the unquenched signal count by an equation:

$$\% \text{Quench} = \left(1 - \frac{\text{Modulated Signal Counts}}{\text{Unquenched Signal Counts}}\right) \times 100\%; \text{ and}$$

wherein said % quench effect is associated with said reference of said step (f) to provide a determination of the presence or the amount of said analyte.

18. An assay according to claim 17 wherein said first reagent comprises an aqueous solution of 0.1N nitric acid in from 0.5% to 1% hydrogen peroxide and said second reagent comprises an aqueous solution of 0.25N sodium hydroxide and a surfactant present in an amount ranging from about 0.1% to about 1% (v/v), based on the total volume of the aqueous second reagent.

19. A non-separation specific binding assay to detect or quantify an analyte in a sample, said assay comprising in the order stated:
   (a) incubating a solution comprising a sample; a solid phase comprising a metal oxide coupled to an analyte or analyte analogue specific to said analyte; and a tracer comprising a specific binding partner to said analyte or analyte analogue having attached thereto an acridinium or benzacridinium ester;
   (b) allowing said solution to react to form a reaction mixture comprising a specific binding complex comprising said tracer bound to said solid phase and a free fraction comprising unreacted tracer;
   (c) contacting said reaction mixture with a first activating reagent comprising an acidic hydrogen peroxide solution;
   (d) contacting said mixture of step (c) with a second activating reagent comprising a basic aqueous solution to provide a modulated chemiluminescent signal;
   (e) measuring said modulated chemiluminescent signal;
   (f) associating said modulated signal with a reference to determine the amount or presence of said analyte in said samples
      wherein said modulated signal is the total chemiluminescent signal from the reaction mixture including the quenched chemiluminescent signal contributed by the tracer that is bound to the solid phase and the chemiluminescent signal from any tracer remaining in said free fraction;
      wherein the amount of tracer of said step (a) is separately activated to emit a chemiluminescent light emission that is measured in the absence of said solid phase resulting in a unquenched signal count measurement;
      wherein a % quench effect is calculated using said modulated signal of said step (e) and the unquenched signal count by an equation:

$$\% \text{ Quench} = \left(1 - \frac{\text{Modulated Signal Counts}}{\text{Unquenched Signal Counts}}\right) \times 100\%; \text{ and}$$

wherein said % quench effect is associated with said reference of said step (f) to provide a determination of the presence or the amount of said analyte.

20. An assay according to claim 19 wherein said first reagent comprises an aqueous solution of 0.1N nitric acid in from 0.5% to 1% hydrogen peroxide and said second reagent comprises an aqueous solution of 0.25N sodium hydroxide and a surfactant present in an amount ranging from about 0.1% to about 1% (v/v), based on the total volume of the aqueous second reagent.

21. A non-separation specific binding assay to detect or quantify an analyte in a sample, said assay comprising, in the order stated:
   (a) incubating a solution comprising a sample; a solid phase which comprises a metal oxide and to which is coupled a first binding partner specific to said analyte; and a tracer comprising a second binding partner to said analyte having attached thereto an acridinium or benzacridinium ester, wherein said first and second binding partner may be the same or different;
   (b) allowing said solution to react to form a reaction mixture comprising a specific binding complex comprising said tracer bound to said analyte which is bound to said solid phase and a free fraction comprising unreacted tracer;
   (c) contacting said reaction mixture with a first activating reagent comprising an acidic hydrogen peroxide solution;
   (d) contacting said mixture of step (c) with a second activating reagent comprising a basic aqueous solution to provide a modulated chemiluminescent signal;
   (e) measuring said modulated chemiluminescent signal; and
   (f) associating said modulated signal with a reference to determine the amount or presence of said analyte in said sample;
      wherein said modulated signal is the total chemiluminescent signal from the reaction mixture including the quenched chemiluminescent signal contributed by the tracer that is bound to the solid phase and the chemiluminescent signal from any tracer remaining in said free fraction;
      wherein the amount of tracer of said step (a) is separately activated to emit a chemiluminescent light emission that is measured in the absence of said solid phase resulting in a unquenched signal count measurement;
      wherein a % quench effect is calculated using said modulated signal of said step (e) and the unquenched signal count by an equation:

$$\% \text{ Quench} = \left(1 - \frac{\text{Modulated Signal Counts}}{\text{Unquenched Signal Counts}}\right) \times 100\%; \text{ and}$$

wherein said % quench effect is associated with said reference of said step (f) to provide a determination of the presence or the amount of said analyte.

22. An assay according to claim 21 wherein said first reagent comprises an aqueous solution of 0.1N nitric acid in from 0.5% to 1% hydrogen peroxide and said second reagent comprises an aqueous solution of 0.25N sodium hydroxide and a surfactant present in an amount ranging from about 0.1% to about 1% (v/v), based on the total volume of the aqueous second reagent.

* * * * *